(12) United States Patent
Chuah et al.

(10) Patent No.: US 8,858,886 B1
(45) Date of Patent: Oct. 14, 2014

(54) SCANNING SYSTEM WITH INTERCHANGEABLE OPTICAL CARTRIDGES FOR FLUORESCENCE MEASUREMENTS

(71) Applicant: Agilent Technologies, Inc., Loveland, CO (US)

(72) Inventors: Yuen Chang Chuah, Penang (MY); Thean Ho Lee, Penang (MY); It Loon Chong, Penang (MY); Wei Yan Lee, Penang (MY)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/890,047

(22) Filed: May 8, 2013

(51) Int. Cl.
*G01N 21/00* (2006.01)
*G01N 21/64* (2006.01)
*G01J 3/02* (2006.01)
*C12M 1/34* (2006.01)
*G01N 21/27* (2006.01)
*G01N 21/93* (2006.01)
*G01N 35/00* (2006.01)
*G01J 3/44* (2006.01)

(52) U.S. Cl.
CPC .......... *G01N 21/6486* (2013.01); *G01N 21/274* (2013.01); *G01N 21/93* (2013.01); *G01N 21/645* (2013.01); *G01N 2035/00326* (2013.01); *G01J 3/4406* (2013.01); *G01J 3/0291* (2013.01)
USPC .................... 422/82.05; 422/68.1; 422/82.08; 435/288.3; 435/288.7

(58) Field of Classification Search
CPC ................. G01N 2035/00326; G01N 21/645; G01N 21/93; G01N 21/274; G01N 21/6486; G01J 3/291; G01J 3/4406
See application file for complete search history.

(56) References Cited

U.S. PATENT DOCUMENTS

| | | | |
|---|---|---|---|
| 7,148,043 B2 | 12/2006 | Kordunsky et al. | |
| 7,183,103 B2 | 2/2007 | Gambini et al. | |
| 7,289,217 B2 | 10/2007 | Boege et al. | |
| 7,452,507 B2 | 11/2008 | Renzi et al. | |
| 7,507,575 B2 | 3/2009 | Bedingham et al. | |
| 7,527,763 B2 | 5/2009 | Bedingham et al. | |
| 7,667,193 B2 | 2/2010 | Finlay | |
| 8,182,767 B2 | 5/2012 | Padmanabhan et al. | |
| 2007/0009382 A1 | 1/2007 | Bedingham et al. | |
| 2007/0183931 A1* | 8/2007 | Stock et al. | 422/82.05 |
| 2007/0248494 A1* | 10/2007 | Mokelke et al. | 422/82.08 |
| 2011/0039274 A1 | 2/2011 | Ludowise | |
| 2011/0289374 A1 | 11/2011 | Suzuki et al. | |
| 2012/0171677 A1 | 7/2012 | Ludowise | |
| 2012/0293796 A1 | 11/2012 | Ludowise et al. | |

* cited by examiner

*Primary Examiner* — Neil N Turk

(57) ABSTRACT

The fluorescence measurement system includes a host apparatus and a self-contained, multichannel optical cartridge. The host apparatus includes a well plate receptacle, and a stage having optical cartridge receptacles that are elongate along one axis of the well plate. The stage and the well plate receptacle are movable relative to one another in the direction of the other axis of the well plate. The optical cartridge engages with the optical cartridge receptacle and includes a linear array of optical assemblies each including an excitation light source, and an emission light detector to generate an intensity signal. The optical cartridge also includes, a memory to store calibration information for each optical assembly. The host apparatus additionally includes a processor to correct the intensity signal from each optical assembly of the optical cartridge using the calibration information received from the optical cartridge for the optical assembly.

22 Claims, 10 Drawing Sheets

SCANNING SYSTEM WITH INTERCHANGEABLE OPTICAL CARTRIDGES FOR FLUORESCENCE MEASUREMENTS

BACKGROUND

Multi-well plates are used to perform various biological, chemical or biochemical assays. A multi-well well plate is composed of a two-dimensional array (e.g., 12×8) frustoconical wells extending into, and typically through, a planar plate from a major surface of the plate. Liquid specimens such as blood, plasma, serum, urine and various reagents are placed into the wells. In some instances, it is desired to monitor the progress of the reactions taking place in the wells. One way to do this is to attach a fluorescent dye to one of the participants in the reaction. The wells are irradiated with excitation light of a wavelength that stimulates the fluorescent dye and the intensity of resulting emission light is measured.

One type of analysis performed in multi-well well plate is a real-time polymerase chain reaction (qPCR) that may be used in DNA sequencing, DNA cloning, gene mapping, and other forms of nucleic acid sequence analysis. In general, qPCR relies on the ability of DNA-copying enzymes to remain stable at high temperatures. A specimen containing DNA molecules is placed in one or more wells of the well plate together with various reagents including a DNA-binding fluorescent dye. The well plate is heated to over 90° C. to break the bonds between the two strands that constitute the DNA molecules in the specimen. The well plate is next cooled to about 0° C. At this temperature, primers bind to the ends of the strands. Finally, the well plate is heated to about 75° C. At this temperature, nucleotides add to the primers and eventually a complementary copy of the DNA template is formed. Binding to the DNA molecule activates the fluorescent dye. Consequently, the intensity of the emission light output by the activated fluorescent dye provides a measure of the amount of the fluorescent dye that has been activated, and, hence, the number of DNA molecules that have been produced.

Conventional instruments for measuring the intensity of the emission light generated by the activated fluorescent dye in qPCR and other reactions monitored by fluorescent dyes use such devices as cameras, photodiodes and photomultipliers to detect the light emitted by the fluorescent dye. Such conventional instruments are configured to work with a specific fluorescent dye, i.e., the instrument generates excitation light at the specified excitation wavelength of the specified fluorescent dye and includes narrow-band emission light filters at the specified emission wavelength of the specified fluorescent dye. This limits the instrument to use with the specified dye. The instrument cannot be used with newer, better, fluorescent dyes that are later introduced. Moreover, different fluorescent dyes cannot be used in different wells of the multi-well plate in a camera-based instrument because all the emission light passes through a single emission filter. Photodiode- and photomultiplier-based instruments are also limited to specific fluorescent dyes, and additionally cannot make simultaneous measurements in multiple wells because such instruments use an X-Y mechanical scanner to align the optical system with the wells of the well plate sequentially.

Additionally, conventional instruments for measuring the intensity of the emission light generated by a fluorescent dye require regular calibration. A conventional instrument has to be taken off-line for calibration and is not available to be used to perform measurements while it is being calibrated.

Accordingly, what is needed is an instrument for measuring the intensity of the emission light generated by an activated fluorescent dye during, for example, qPCR that can be used with multiple different fluorescent dyes, including fluorescent dyes that are not commercially available at the time the instrument is manufactured, that can measure the intensity of the fluorescent light in multiple wells simultaneously, that can measure the intensity of the fluorescent light generated by different fluorescent dyes sequentially, and that does not require the instrument to be taken off-line for calibration.

DETAILED DESCRIPTION

Figure 1A:
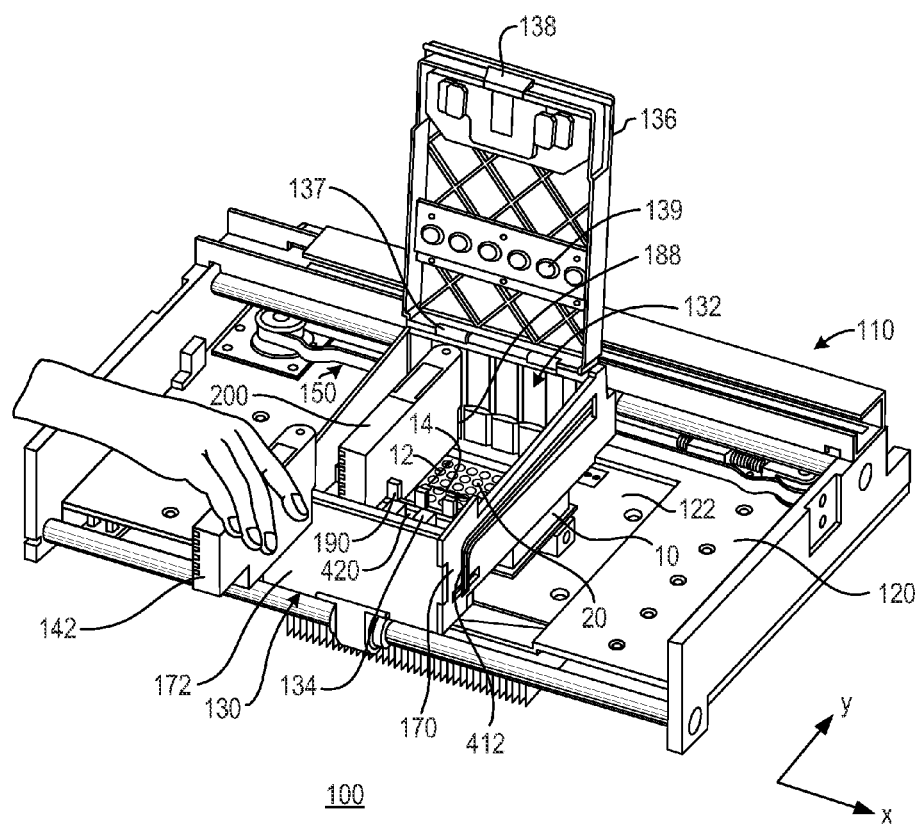
FIGS. 1A and 1B are perspective views showing an example of a fluorescence measurement system.

Disclosed herein is a fluorescence measurement system for performing fluorescence measurements on a multi-well well plate having wells arranged in a rectangular array having a first axis and a second axis, orthogonal to the first axis. The system includes a host apparatus and one or more self-contained, multichannel optical cartridges. The host apparatus includes a well plate receptacle to receive the well plate, and a stage having at least one optical cartridge receptacle. The optical cartridge receptacle is elongate in a first direction, parallel to the first axis of the well plate received by the well plate receptacle. The optical cartridge receptacle includes an electrical connector. At least one of the stage and the well plate receptacle is movable relative to the other of the stage and the well plate receptacle in a second direction, parallel to the well plate and to the second axis of the well plate. The optical cartridge is configured to engage with the optical cartridge receptacle and includes a linear array of optical assemblies. Each of the optical assemblies includes a respective excitation light source to generate excitation light for output to a respective well of the well plate and a respective emission light detector to generate an emission light intensity signal in response to emission light received from the respective well of the well plate. The optical cartridge additionally includes a memory to store respective calibration information for each of the optical assemblies, and an electrical connector electrically coupled to the memory and to each of the optical assemblies and configured to connect to the electrical connector of the optical cartridge receptacle. The host apparatus additionally includes a processor to correct the emission light intensity signal received from each optical assembly of the optical cartridge using the respective calibration information received from the optical cartridge for the optical assembly.

The fluorescence measurement system produces measurements from multiple wells of the well plate that have well-to-well uniformity that is not degraded by differences the component parts of the optical cartridge, including excitation light source, emission light detector, and optical assemblies. The corrected emission light intensity signals are effectively uniform between optical assemblies within the same optical cartridge as well as between different optical cartridges.

Also disclosed herein is a self-contained, multichannel optical cartridge for installation into a host apparatus to perform fluorescence measurements on a multi-well well plate having wells arranged in a linear array in which the wells are offset from one another by a pitch. The optical cartridge includes optical assemblies arranged in a linear array, and offset from one another by a pitch equal to the pitch of the wells, a memory, and an electrical connector. Each of the optical assemblies includes a respective excitation light source to generate excitation light for output from the optical cartridge, a respective light source driver to provide current to the excitation light source in accordance with an intensity control signal, and a respective emission light detector to generate an emission light intensity signal in response to emission light received by the optical cartridge. The emission light differs in wavelength from the excitation light and is superposed on the excitation light. The memory is to store respective calibration information for each of the optical assemblies. The calibration information includes an intensity control signal. The electrical connector is located at an external surface of the optical cartridge, and provides electrical connections that include an electrical connection to output the calibration information stored in the memory of the optical cartridge to the host apparatus; an electrical connection to receive the intensity control signal from the host apparatus; and a respective electrical connection to output the electrical signal from the emission light detector of each of the optical assemblies to the host apparatus.

Figure 1B:
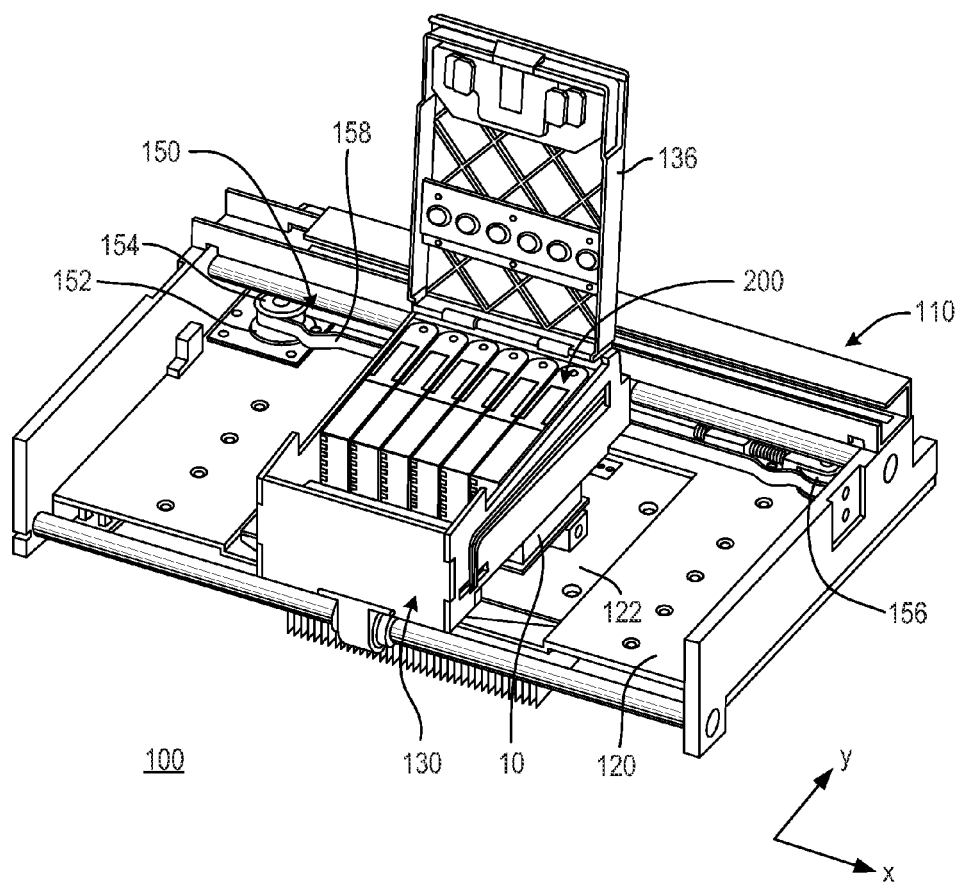

FIGS. 1A and 1B are perspective views showing an example 100 of a fluorescence measurement system for performing fluorescence measurements on a multi-well well plate as disclosed herein. Fluorescence measurement system 100 includes a host apparatus 110 and at least one optical cartridge 200. The example of host apparatus 110 shown in FIGS. 1A and 1B is capable of accommodating as many as six optical cartridges 200. FIG. 1A shows system 100 with a first optical cartridge 200 installed and a second optical cartridge 142 in the process of being installed. FIG. 1B shows system 100 with all six optical cartridges 200 installed.

In the example shown, host apparatus 110 includes a chassis 120. In the example shown, chassis 120 is substantially rectangular and has long sides and short sides that respectively define an x-direction and a y-direction that will be used to denote directions in the following description. Mounted substantially in the center of chassis 120 is a well plate receptacle 122 configured to locate a standard multi-well well plate 10. In some examples, well plate receptacle 122 locates well plate 10 in a recess defined in the well plate receptacle. In other examples, well plate receptacle 122 locates well plate 10 by part of the well plate receptacle being received in a recess in the back of the well plate. A well plate receptacle is alternatively referred to as a sample well, a sample block, a sample holder, a plate holder, or a thermal block. Some embodiments additionally include a so-called hot-top or heated lid assembly (not shown) located on the major surface of well plate 10 remote from well plate receptacle 122 to assist in seating well plate 10 on well plate receptacle 122, and to prevent condensation forming on the major surface of the well plate during thermal cycling.

In the example shown, well plate 10 is a 96-well plate having a rectangular array of 12×8 wells extending into, and, typically, through the well plate from the major surface of the well plate. An exemplary well of the well plate 10 is shown at 20. Reference numeral 20 will additionally be used to refer to the wells of well plate 10 collectively. Well plate receptacle 122 locates well plate 10 such that the wells arrayed along a first axis 12 of the array are parallel to the y-direction, and the wells arrayed along a second axis 14 of the array, and orthogonal to the first axis, are parallel to the x-direction. Other examples of host apparatus 110 are configured to operate with well plates having rectangular (or square) arrays of different numbers of wells from those of exemplary well plate 10. For example, another configuration of well plate 10 may have more wells arrayed along the first axis than along the second axis.

Host apparatus 110 additionally includes a stage 130 that is mounted relative to well plate receptacle 122 in a manner that allows at least one of stage 130 and well plate receptacle 122 to move relative to the other of the stage and the well plate receptacle in a direction parallel to the second axis 14 of well plate 10 received by well plate receptacle 122. In the example shown, stage 130 is mounted in a manner that allows it to move in the x-direction relative to well plate receptacle 122. An actuator 150 (FIG. 1B) mounted on chassis 120 is coupled to stage 130 to move stage 130 back and forth in the x-direction relative to well plate receptacle 122.

Figure 1C:
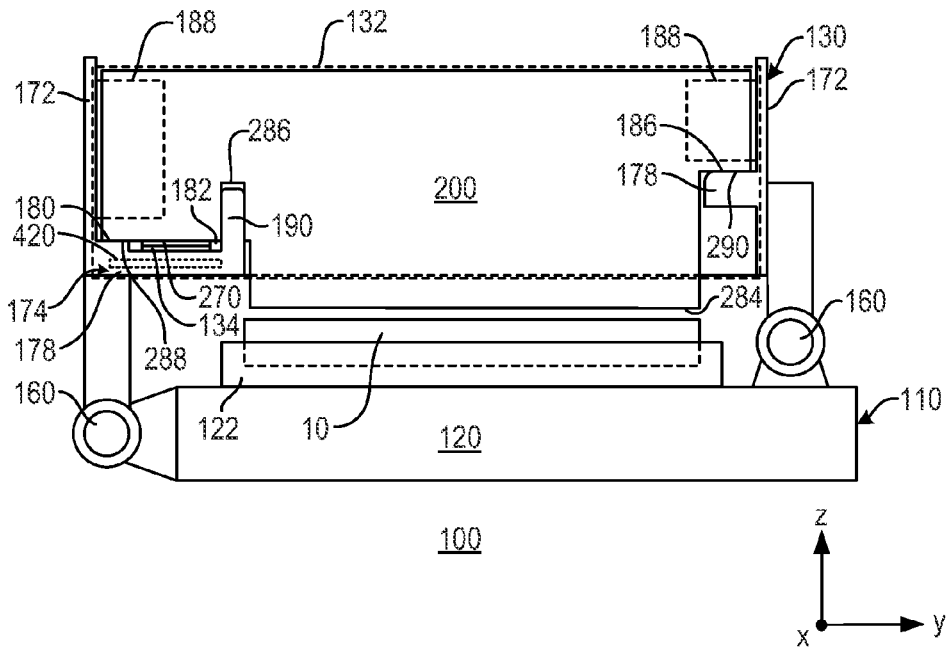
FIGS. 1C and 1D are respectively a side view and a plan view of the stage of the fluorescence measurement system.
Figure 1D:
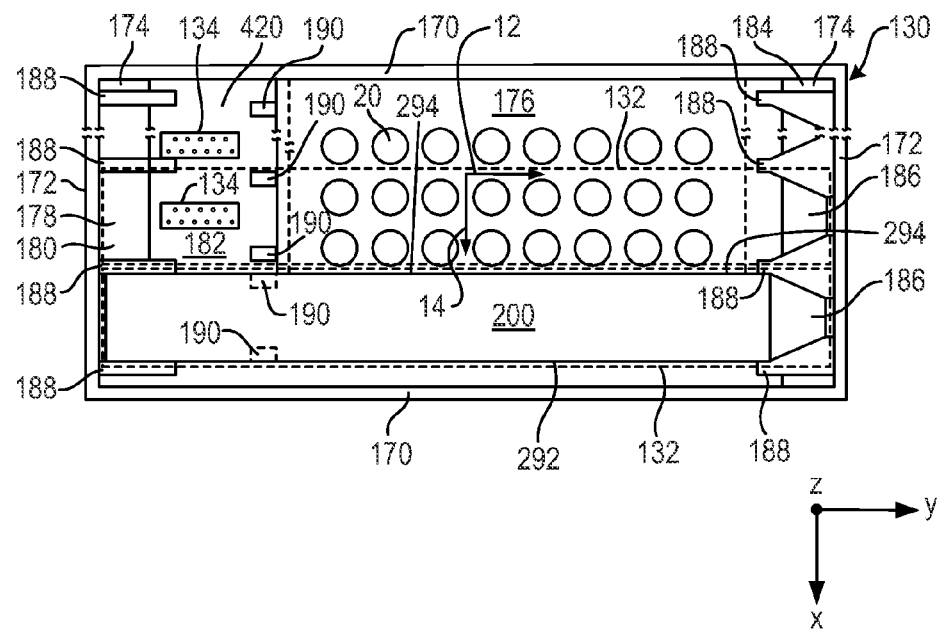

FIGS. 1C and 1D are respectively a side view and a plan view of stage 130. In FIG. 1C, one of the sidewalls of the stage has been removed to show an optical cartridge (described below) installed in the stage and part of the internal structure of the stage. In FIG. 1D, several of the optical cartridge receptacles (described below) have been omitted to simplify the drawing.

Referring to FIGS. 1A-1D, stage 130 includes at least one optical cartridge receptacle 132. In the example shown in FIGS. 1A and 1B, stage 130 includes six optical cartridge receptacles linearly arrayed in the x-direction, parallel to the direction of movement of stage 130. Other examples have more than or fewer than six optical cartridge receptacles linearly arrayed in the x-direction. Each optical cartridge receptacle 132 is configured to accommodate a respective optical cartridge 200. Each optical cartridge receptacle 132 is elongate in the y-direction, parallel to the first axis 12 of the array of wells 20 in well plate 10 located by well plate receptacle 122, and orthogonal to the direction of movement of stage 130.

The optical cartridge receptacles 132 are typically offset from one another in the x-direction by a pitch equal to an integer multiple of the pitch of the wells arrayed along the second axis 14 of the array of wells 20 in well plate 10. This allows system 100 to use multiple optical cartridges to perform simultaneous fluorescence readings on multiple groups of wells (i.e., rows or columns of wells, depending on the orientation of the well plate relative to the direction of movement of stage 130) arrayed along the first axis 12 of the well plate. System 100 can also move stage 130 in the x-direction to perform simultaneous fluorescence readings on the groups of wells located between the groups of wells with which the optical cartridges were initially aligned.

In an example in which the offset between adjacent optical cartridge receptacles 132 in stage 130 is equal to twice the pitch of the wells 20 arrayed along the second axis 14 of well plate 10, by using six optical cartridges all of the same type, system 100 can perform simultaneous fluorescence measurements on half of the wells in the well plate. Then, by moving stage 130 a distance equal to the pitch of wells along second axis 14, system 100 can perform simultaneous fluorescence measurements on the remaining half of the wells. In another example with the same offset between adjacent optical cartridge receptacles, by using three optical cartridges of one type interleaved with three optical cartridges of another type, system 100 can perform simultaneous fluorescence measurements on a first set of wells composed of one fourth of the wells in the well plate using a first fluorescent dye and a second set of wells composed of one fourth of the wells in the well plate using a second fluorescent dye. Then, by moving stage 130 a distance equal to the pitch of the wells along second axis 14, system 100 can perform simultaneous fluorescence measurements on a third set wells composed of one fourth of the wells in the well plate using the first fluorescent dye and on a fourth set of wells composed of one fourth of the wells in the well plate using the second fluorescent dye. Many other arrangements of optical cartridges of different types in stage 130 are possible and may be used.

Each optical cartridge receptacle 132 includes a respective electrical connector 134 at a surface of the optical cartridge receptacle. Electrical connector 134 is connected to receive power and signals from host apparatus 110 and to output signals to host apparatus 110. In the example shown, electrical connector 134 is a multi-pin electrical connector. Other examples use a different type of electrical connector as electrical connector 134.

Figure 2A:
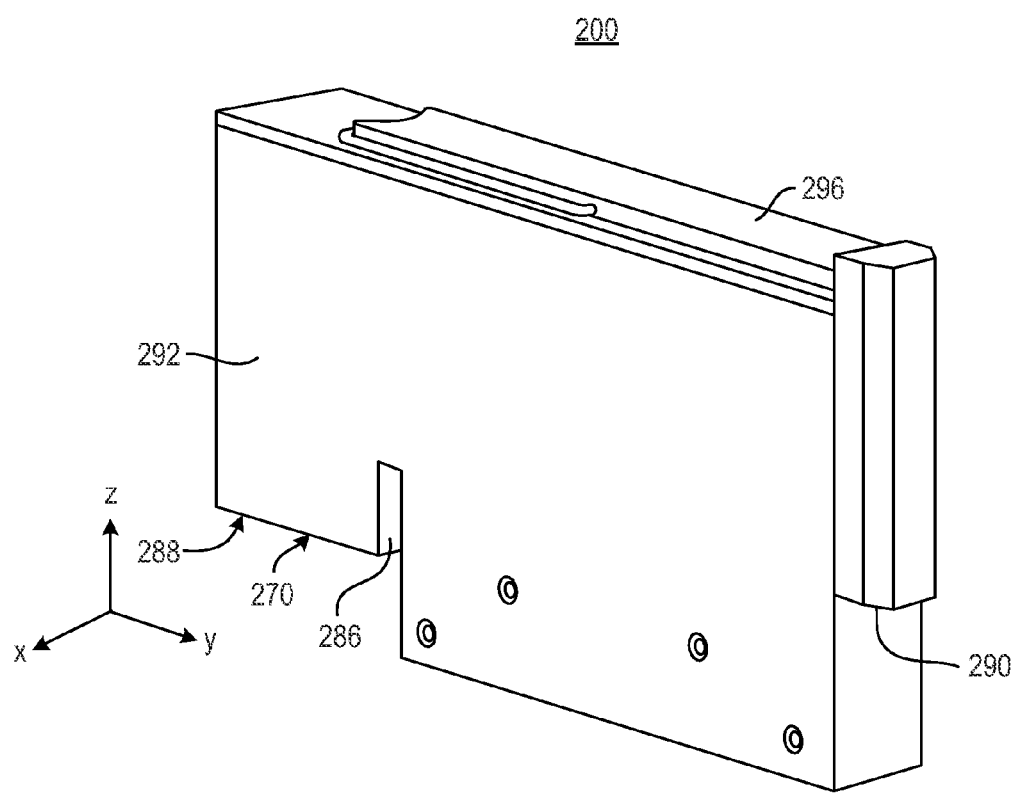
FIG. 2A is a perspective view showing the exterior of an example of an optical cartridge of the fluorescence measurement system.
Figure 2B:
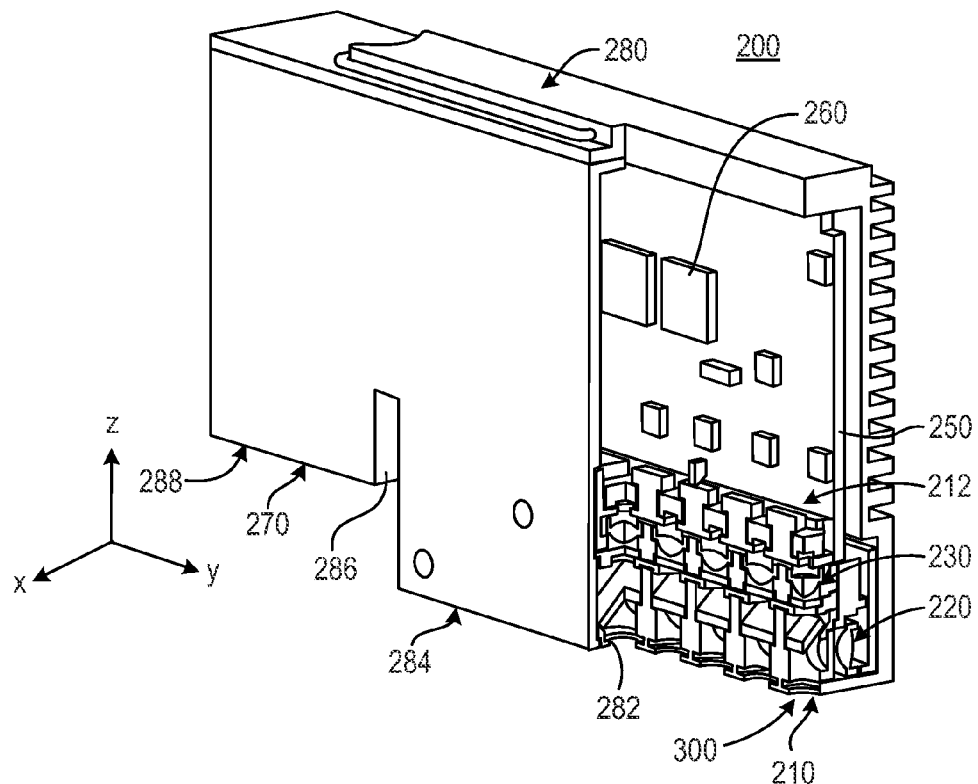
FIG. 2B is a perspective, cutaway view of the optical cartridge.
Figure 2C:
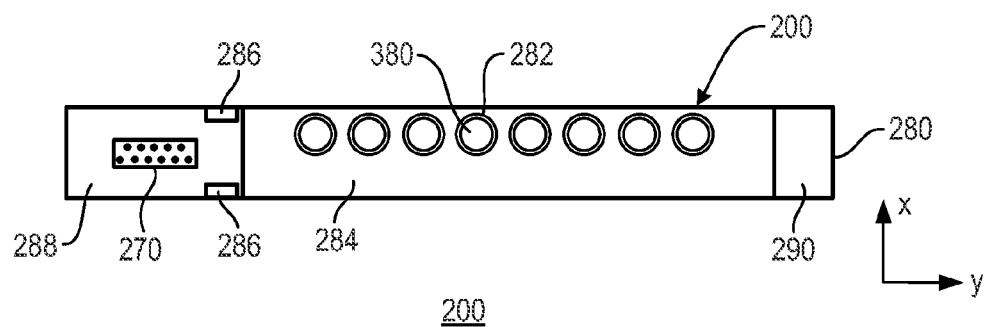
FIG. 2C is a view of the face of the optical cartridge that faces the well plate.

FIG. 2A is a perspective view showing the exterior of an example of optical cartridge 200 in greater detail. FIG. 213 is a perspective, cutaway view of optical cartridge 200. FIG. 2C is a view of the face of optical cartridge 200 that faces the well plate receptacle when the optical cartridge is installed in stage 130. Referring to FIGS. 2A-2C and additionally to FIG. 1A, optical cartridge 200 is a self-contained, multichannel optical cartridge configured to engage with the optical cartridge receptacle 132 of stage 130. Optical cartridge 200 is self-contained in the sense that, when a given optical cartridge 200 is installed in any of the optical cartridge receptacles 132 of host apparatus 110, the electro-optical performance of the optical cartridge is independent of the host apparatus. Self-contained optical cartridge 200 can be calibrated independently of any host apparatus 110 with which it is used. Consequently, calibration of optical cartridge 200 does not require that the host apparatus be taken off-line: the host apparatus can continue to be used in production with a spare optical cartridge installed in place of the optical cartridge being calibrated.

Optical cartridge 200 is elongate in the same direction as the optical cartridge receptacles 132 of stage 130 of host apparatus 110. Optical cartridge 200 will be described as oriented when installed in stage 130. Thus, optical cartridge 200 is elongate in the y-direction.

Optical cartridge 200 includes a linear array of optical assemblies. An exemplary optical assembly is shown at 210. Reference numeral 210 will be used to refer to the optical assemblies collectively. Optical assemblies 210 typically and in the example shown correspond in number to the wells 20 arrayed along the first axis 12 of well plate 10. In other examples, the optical assemblies correspond in number to a subset, e.g., half, of the wells arrayed along first axis 12. Optical assemblies 210 are offset from one another in the elongate direction of optical cartridge 200 by a pitch equal to the pitch of the wells 20 along the first axis 12 of well plate 10.

As will be described in more detail below with reference to FIG. 3A, each optical assembly 210 includes a respective excitation light source 220 to generate excitation light for output to a respective well 20 of well plate 10 with which the optical assembly is aligned, and a respective emission light detector 230 to generate an emission light intensity signal in response to emission light received from the respective well 20 of well plate 10 with which the optical assembly is aligned. Providing optical assemblies corresponding in number to the wells arrayed along the first axis 12 of the well plate, and offset from one another by a pitch equal to the pitch of the wells along the first axis 12 of the well plate, with each optical assembly including its own excitation light source and emission light detector allows optical cartridge 200 to perform simultaneously fluorescence measurements on all the wells (or on a subset of the wells) in a linear array parallel to the first axis 12 of the well plate.

Optical cartridge 200 additionally includes a non-volatile memory 260 to store respective calibration information for each of the optical assemblies 210 in the optical cartridge. Installation of the optical cartridge 200 in one of the optical cartridge receptacles 132 in stage 130 of host apparatus 110 causes the optical cartridge to download the calibration information to the host apparatus. The host apparatus then uses the respective calibration information for each optical assembly to correct the respective emission light intensity signal received from the optical assembly to generate a corrected emission light intensity signal that is output from the host apparatus. As will be described in greater detail below, in some embodiments, the calibration information is additionally used to control the intensity of the excitation light output by the optical cartridge. In such embodiments, the calibration information may be used to control the intensity of the excitation light output by all of the optical assemblies of the optical cartridge or may be used to individually control the intensity of the excitation light output by each of the optical assemblies.

Optical cartridge 200 includes an electrical connector 270 electrically coupled to non-volatile memory 260 and to each of the optical assemblies 210 constituting the optical cartridge. Electrical connector 270 is configured to connect to the electrical connector 134 of any one of the optical cartridge receptacles 132 of stage 130. In the example shown, electrical connector 270 is a multi-pin electrical connector that connects to the multi-pin electrical connector used as electrical connector 134 in optical cartridge receptacle 132. Other types of electrical connector may be used as electrical connectors 134 and 270. When optical cartridge 200 is installed in one of the optical cartridge receptacles 132 in stage 130, host apparatus 110 outputs power and signals to optical cartridge 200 and optical cartridge 200 outputs signals to host apparatus 110 via electrical connectors 134 and 270.

Referring again to FIGS. 1A-1D, host apparatus 110 additionally includes a processor 510 (not shown, but described below with reference to FIG. 5) to which the electrical connector 134 of each optical cartridge receptacle 132 is connected. When installed in a given optical cartridge receptacle 132 of stage 130, optical cartridge 200 outputs the calibration information stored in its non-volatile memory 260 for each optical assembly 210. The calibration information passes through electrical connectors 270 and 134 to the processor. The processor corrects the emission light intensity signal received from each optical assembly 210 of optical cartridge 200 via connectors 270 and 134 using the respective calibration information for the optical assembly received from optical cartridge 200.

Figure 3A:
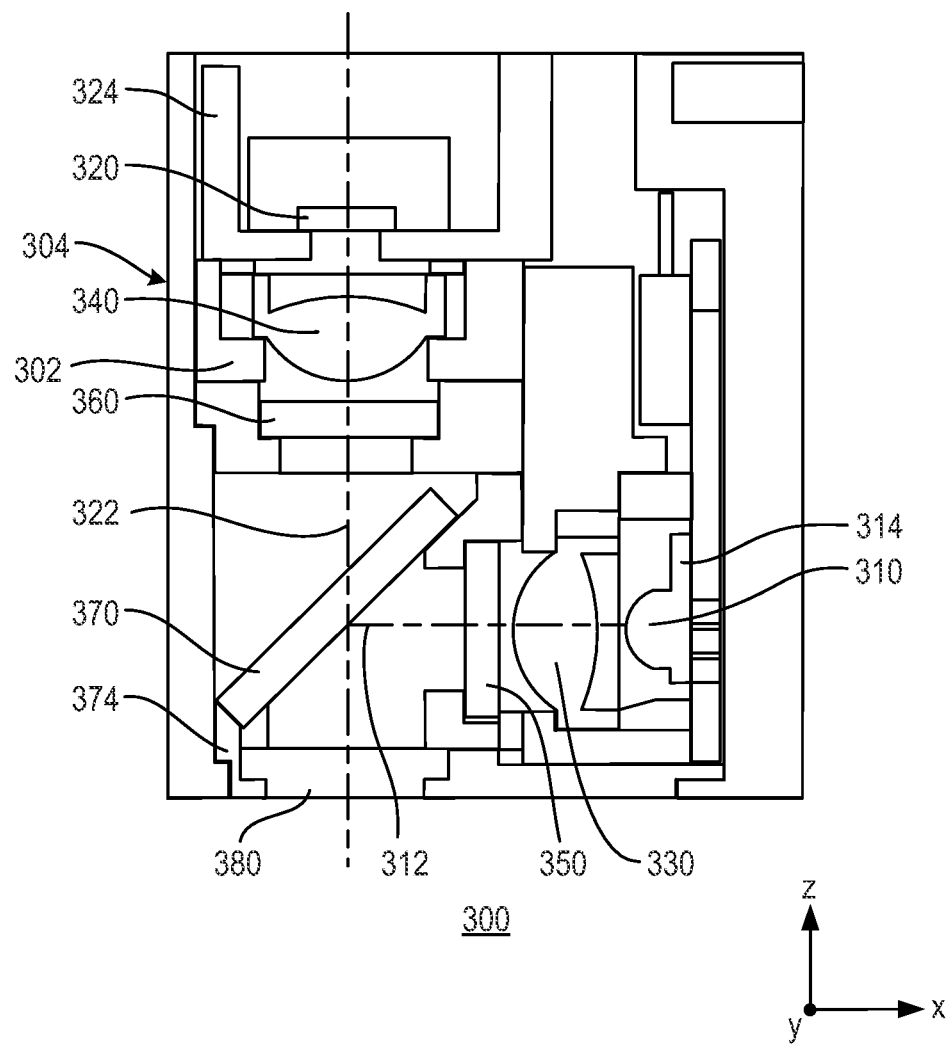
FIG. 3A is an enlarged view showing an example of an optical module of the optical cartridge.

FIG. 3A is an enlarged view of an example 300 of an optical module that constitutes part of one of the optical assemblies 210 of optical cartridge 200. Optical module 300 and associated electrical circuitry 600 that will be described below with reference to FIG. 6 together to form a respective optical assembly 210. The remaining optical assemblies 210 of optical cartridge 200 include respective optical modules similar to optical module 300 and associated electrical circuitry 600. Optical module 300 is specified for use with a particular fluorescent dye having a specified excitation spectrum and a specified emission spectrum. System 100 can be configured to operate with one or more additional fluorescent dyes (existing or new) with which it is currently not configured to operate simply by purchasing and installing in stage 130 one or more new optical cartridges 200 each of which includes optical modules 300 configured to operate with such additional fluorescent dye(s). Purchase of such additional optical cartridges prevents obsolescence of the system.

Optical module 300 is configured to irradiate the specified fluorescent dye with excitation light in a narrow range of wavelengths at or near the peak of the specified excitation spectrum and to measure the intensity of emission light generated by the fluorescent dye in response to the excitation light in a narrow range of wavelengths at or near peak of the specified emission spectrum.

In typical embodiments of optical cartridge 200, the respective optical modules 300 of all of the optical assemblies 210 of the optical cartridge are configured to operate with the same fluorescent dye. However, in some embodiments of optical cartridge 200, the respective optical modules of one or more of the optical assemblies 210 are configured for use with one fluorescent dye and the respective optical modules of one or more others of the optical assemblies 210 are configured for use with one or more other fluorescent dyes to enable optical cartridge 200 to monitor reactions using different fluorescent dyes at the same time.

Optical module 300 includes an excitation light emitter 310, an emission light sensor 320, a collimating lens 330, a focusing lens 340, an excitation light bandpass filter 350, an emission light bandpass filter 360 and a beam splitter 370. Excitation light emitter 310, together with a current source, an example of which is described below with reference to FIG. 6, constitute excitation light source 220. Emission light sensor 320, together with a detector circuit, an example of which is described below with reference to FIG. 6, constitute emission light detector 230. Excitation light emitter 310 has an optical axis 312 and emission light sensor 320 has an optical axis 322. Excitation light emitter 310 and emission light sensor 320 are arranged so that optical axes 312, 322 intersect substantially orthogonally. Optical module 300 additionally has a light input/output port 380. Optical module 300 emits excitation light generated by excitation light emitter 310 through light input/output port 380 to a well 20 with which the optical module is aligned. Optical module 300 receives emission light generated in the well 20 aligned with the optical module through light input/output port 380. In the example shown, light input/output port 380 is aligned with the optical axis 322 of emission light sensor 320. The excitation light and the emission light are superposed at light input/output port 380.

Typically, a light-emitting diode (LED) is used as excitation light emitter 310 and a photo diode is used as emission light sensor 320. Other light emitters may be used as excitation light emitter 310. Other light sensors may be used as emission light sensor 320. The LED used as excitation light emitter 310 is one that generates light in a band of wavelengths that includes the excitation spectrum of the fluorescent dye with which the optical cartridge 200 of which optical module 300 constitutes part is specified to operate. The photo diode used as emission light sensor 320 is typically a silicon photo diode.

Collimating lens 330 and focusing lens 340 are typically aspherical convex lenses. Excitation light bandpass filter 350 and emission light bandpass filter 360 are typically dichroic filters having narrow pass bands. The passband of excitation light bandpass filter 350 is nominally centered on the peak of the excitation spectrum and passband of the emission light bandpass filter 360 is nominally centered on the peak of the emission spectrum of the fluorescent dye with which the optical cartridge of which optical module 300 constitutes part is specified to operate. Excitation light bandpass filter 350 selects light in a narrow band of wavelengths substantially centered on the peak of the excitation spectrum from the somewhat broader band of wavelengths generated by the LED used as excitation light emitter 310. Emission light bandpass filter 360 passes light in a narrow band of wavelengths substantially centered on the peak of the emission spectrum to emission light sensor 320 and rejects light of all other wavelengths. Emission light bandpass filter 360 helps prevent ambient light from saturating emission light sensor 320.

Collimating lens 330 is located between excitation light emitter 310 and beam splitter 370 and is spaced from excitation light emitter 310 by a distance substantially equal to its focal length. Arranged as just described, collimating lens 330 collimates the excitation light generated by excitation light emitter 310 into a substantially parallel beam that is emitted via light input/output port 380 towards the well 20 of well plate 10 with which optical module 300 is aligned. Excitation light bandpass filter 350 is located between collimating lens 330 and beam splitter 370.

Focusing lens 340 is located between beam splitter 370 and emission light sensor 320 and is separated from emission light sensor 320 by a distance substantially equal to its focal length. Arranged as just described, focusing lens 340 focuses on emission light sensor 320 the emission light received from the well 20 of well plate 10 with which optical module 300 is aligned via light input/output port 380. Emission light bandpass filter 360 is located between beam splitter 370 and focusing lens 340.

In some embodiments, beam splitter 370 is a dichroic beam splitter having a substrate of a transparent material, such as glass, that supports multiple thin layers of dielectric materials of different refractive indices. The properties of the dielectric layers are chosen to make beam splitter 370 highly reflective in the wavelength band of excitation light bandpass filter 350 and highly transmissive in the wavelength band of the emission light bandpass filter 360. In other embodiments, beam splitter 370 is a partially-silvered mirror that transmits a portion of the excitation light generated by excitation light emitter 310 and transmits a portion of the emission light to emission light sensor 320. In some embodiments, beam splitter 370 reflects about half of the intensity of the excitation light and transmits about half of the intensity of the emission light. In other embodiments, to conserve emission light, beam splitter 370 reflects substantially less than half of the intensity of the excitation light and transmits substantially more than half of the intensity of the emission light. The loss of excitation light is compensated for by increasing the intensity of the excitation light generated by excitation light emitter 310.

Beam splitter 370 is located at the intersection of the optical axes 312, 322 of excitation light emitter 310 and emission light sensor 320 and is oriented at 45° to each optical axis 312, 322. In the example shown, beam splitter 370 reflects at least a portion of the excitation light generated by excitation light emitter 310 towards the well 20 aligned with the optical axis 322 of emission light sensor 320, and transmits at least a portion of the emission light received from well 20 towards emission light sensor 320. In another example, the positions of excitation light emitter 310 and emission light sensor 320 and their respective lenses and filters are interchanged.

Figure 3B:
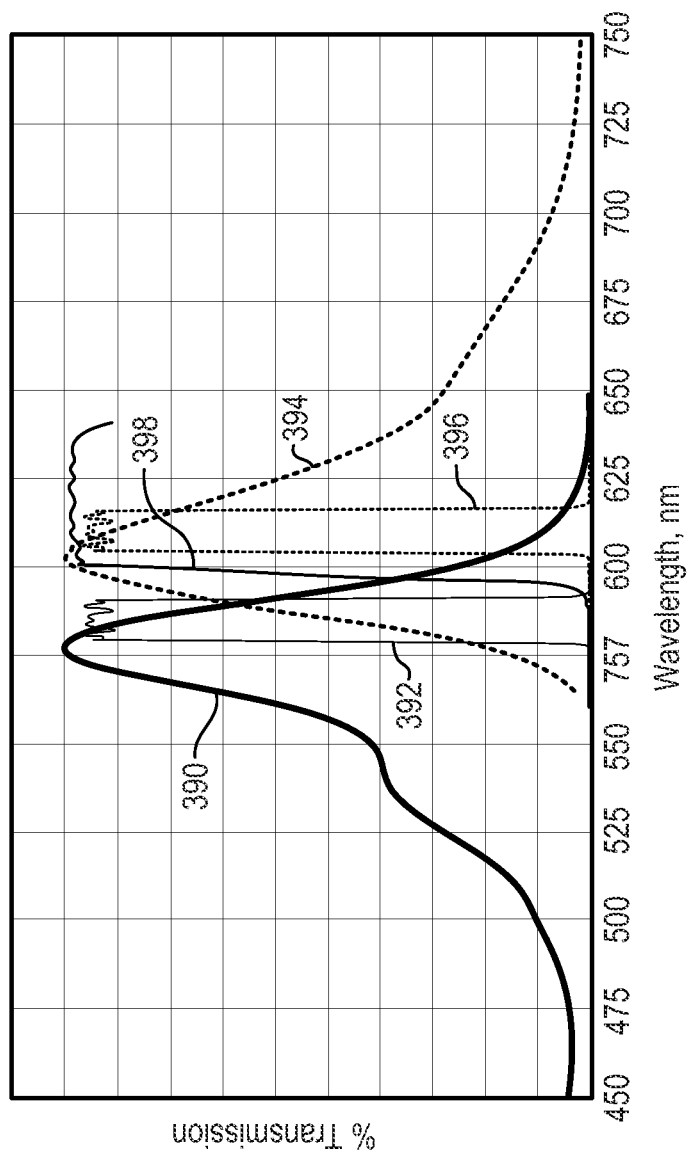
FIG. 3B is a graph showing examples of the spectral responses of the optical components of the optical module.

FIG. 3B is a graph showing examples of the spectral responses of the optical components of an example of an optical module 300 of an optical cartridge specified for use with an exemplary fluorescent dye referred to as ROX. In FIG. 3B, reference numeral 390 indicates the absorption spectrum of the fluorescent dye, reference numeral 392 indicates the transmission spectrum of excitation light bandpass filter 350, reference numeral 394 indicates the emission spectrum of the fluorescent dye, reference numeral 396 indicates the transmission spectrum of emission light bandpass filter 360, and reference numeral 398 indicates the transmission spectrum of an example of beam splitter 370 embodied as a dichroic filter.

In the example shown, each of excitation light emitter 310, emission light sensor 320, collimating lens 330, focusing, lens 340, excitation light bandpass filter 350, emission light bandpass filter 360 and beam splitter 370 is mounted in a respective plastic or metal mount. An exemplary mount, that of focusing lens 340, is shown at 302. Reference numeral 302 will be used herein to refer to the mounts collectively. The mount 314 for the excitation light emitter 310 additionally includes electrical connections (not shown) that connect excitation light emitter 310 to the respective current source that, together with excitation light emitter 310, constitutes excitation light source 220. The mount 324 for emission light sensor 320 additionally includes electrical connections (not shown) that connect emission light sensor 320 to the respective detector circuit that, together with emission light sensor 320, constitutes emission light detector 230. The mount 374 for beam splitter 370 also defines the light input/output port 380 of optical module 300.

Each mount 302 is configured to receive the respective optical component mounted therein in a precisely-defined position relative to the mount. Mounts 302 are also configured to fit together to form an armature 304 in which the relative positions of the mounts are precisely defined. Consequently, the relative positions of excitation light emitter 310, emission light sensor 320, collimating lens 330, focusing lens 340, excitation light bandpass filter 350, emission light bandpass filter 360 and beam splitter 370 are precisely defined in optical module 300. In other examples, the optical components of optical module 300 are directly mounted in a unitary armature.

Referring again to FIG. 2B, optical cartridge 200 includes a printed circuit board 250 on which are mounted optical assemblies 210 arranged in a linear array that extends in the y-direction. The number of optical assemblies depends on the number of wells 20 arrayed along the first axis 12 of the array of wells in well plate 10. The example shown is configured for use with an 8×12 well plate, and optical cartridge 200 has eight optical assemblies 210 arranged in a linear array. In another example configured for use with an 8×12 well plate, optical cartridge has optical assemblies 210 arranged in a linear array. Each optical assembly 210 includes a respective optical module 300 and electrical circuitry 212 associated with the optical module. The circuitry carried by printed circuit board 250 will be described in detail below with reference to FIG. 6.

Printed circuit board 250 and the components mounted thereon are mounted inside an enclosure 280. Enclosure 280 is constructed of an opaque material that excludes ambient light from the optical assemblies 210 of optical cartridge 200. Enclosure 280 defines an array of apertures in a surface 284 that faces well plate receptacle 122 when optical cartridge 200 is installed in one of the optical cartridge receptacles 132 of stage 130. An exemplary aperture is shown at 282. Reference numeral 282 will also be used to refer to the apertures collectively. Each aperture 282 is aligned with the light input/output port 380 of a respective optical module 300 of optical cartridge 200 to allow excitation light generated by excitation light source 220 to be emitted from optical cartridge 200 and to allow emission light to be received by the respective emission light detector 230 within the optical cartridge.

Enclosure 280 has external features configured to engage positively with the optical cartridge receptacles 132 of stage 130. In the example shown, enclosure 280 defines keyways 286 that define the position of optical cartridge 200 in stage 130 in the y-direction, and includes surfaces 288, 290 that define the position of optical cartridge 200 in stage 130 in the z-direction, and side surfaces 292, 294 that define the position of optical cartridge in stage 130 in the x-direction.

Referring additionally to FIGS. 1C and 1D, stage 130 is configured as a hollow, substantially-rectangular, open-topped box. Stage 130 includes opposed sidewalls 170, opposed end walls 172 and a bottom 174 facing well plate receptacle 122. Bottom 174 defines a large aperture 176 dimensioned to allow the portion of each optical cartridge 200 that includes surface 284 to extend through the aperture when the optical cartridge is installed in stage 130. A portion 178 of bottom 174 on one side of aperture 176 includes a surface 180. Surface 180 is substantially planar in the x-y plane, and defines an array of recesses in each of which is located the electrical connector 134 of a respective one of the optical cartridge receptacles 132. An exemplary recess is shown at 182. Electrical connectors 134 are electrically connected to a backplane printed circuit assembly (PCA) 420 that will be described in greater detail below with reference to FIG. 4. Another portion 184 of bottom 174 on the other side of aperture 176 is offset in the z-direction from portion 178 and includes a surface 186. Surface 186 is substantially planar in the x-y plane. Surfaces 180, 186 of stage 130 abut surfaces 288, 290 of optical cartridge 200 to define the location of each optical cartridge 200 in stage 130 in the z-direction.

Stage 130 additionally includes guides within each of its optical cartridge receptacles 132 to define the location and orientation of a respective optical cartridge 200 installed in the optical cartridge receptacle. Lateral guides 188 extend inwardly from each end wall 172 of stage 130 and are offset from one another in the x-direction such that when an optical cartridge is installed in one of the optical cartridge receptacles 132 of stage 130, the lateral guides 188 on opposite sides of the optical cartridge receptacle abut the side surfaces 292, 294 of the optical cartridge to define the location of the optical cartridge in the x-direction. Additionally, within each optical cartridge receptacle 132, a pair of longitudinal guides 190 extends inwardly in the z-direction from bottom portion 178. Longitudinal guides 190 are configured to engage with keyways 286 defined in the enclosure 280 of optical cartridge 200. When an optical cartridge is installed in one of the optical cartridge receptacles 132 of stage 130, the guides 190 within the optical cartridge receptacle engage with the keyways 286 of the optical cartridge to define the location of the optical cartridge in the y-direction.

Stage 130 additionally includes a lid 136 (FIGS. 1A and 1B) attached by a hinge 137 to one of the end walls 172 of stage 130. Lid 136 opens to allow the installation and removal of optical cartridges 200. A latch 138 affixed to the other of the end walls 172 holds lid 136 in its closed position in which compliant bumpers 139 mounted on the lid abut the surface 296 of enclosure 280, remote from surface 284, to urge the surfaces 288, 290 of the optical cartridge 200 into firm contact with surfaces 180, 186, respectively, of stage 130.

The position of printed circuit board 250 inside enclosure 280 is precisely defined so that engagement of enclosure 280 with one of the optical cartridge receptacles 132 of stage 130 precisely defines the locations of the optical modules 300 of the optical cartridge 200 relative to the stage. As will be described in greater detail below, a portion of enclosure 280 in which the optical modules 300 are located and that includes surface 284 is offset in the −z-direction relative to the surfaces 288, 290 of enclosure 280 that engage with surfaces 180, 186, respectively, of stage 130. This enables optical modules 300 to be positioned so that light input/output port 380 is separated from the surface of well plate 10 by a narrow gap, typically only 1-2 mm wide. The close separation between optical cartridge 200 and well plate 10 maximizes light coupling between each well 20 of well plate 10 and the optical module 300 aligned with the well, reduces the coupling of ambient light into the optical assembly, and reduces crosstalk of light between adjacent optical modules 300.

Figure 4:
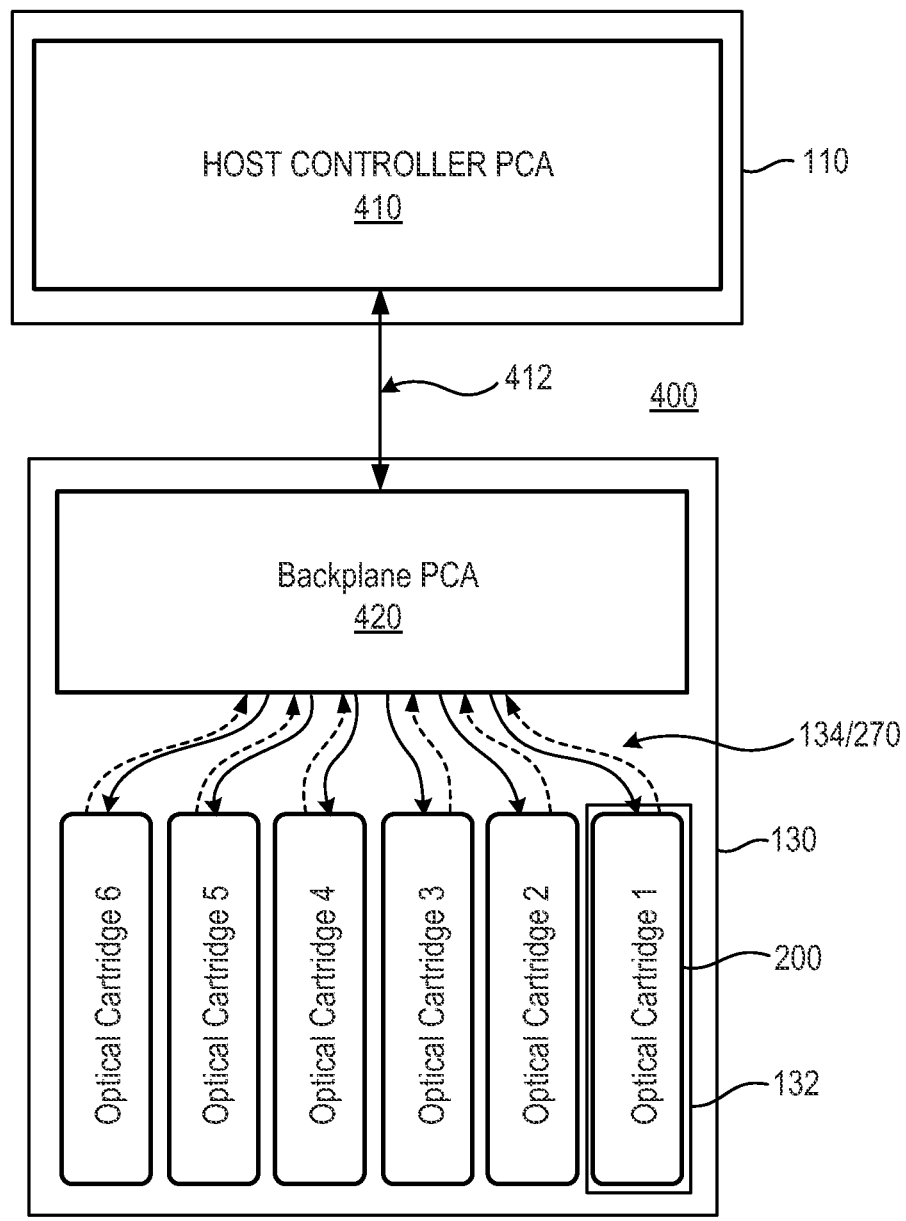
FIG. 4 is a high-level block diagram showing an example of the electrical circuitry of the fluorescence measurement system.

FIG. 4 is a high-level block diagram showing an example 400 of the electrical circuitry of system 100. Host apparatus 110 includes a host controller printed circuit assembly (PCA) 410 that will be described in greater detail below with reference to FIG. 5. Backplane printed circuit assembly (PCA) 420 is mounted on stage 130. A ribbon cable 412 extends between host controller (PCA) 410 and backplane PCA 420 to provide power to the backplane PCA and to provide signal connections between the host controller PCA and the backplane PCA. Ribbon cable 412 is flexible and folded to allow backplane PCA 420 mounted on stage 130 to move back and forth relative to host controller PCA 410 mounted on chassis 120 during operation of system 100. The respective electrical connector 134 in each optical cartridge receptacle 132 of stage 130 is mounted on backplane PCA 420. When an optical cartridge 200 is installed in one of the optical cartridge receptacles 132 of stage 130, the electrical connector 270 of the optical cartridge electrically connects to the electrical connector 134 of the optical cartridge receptacle to supply power to the optical cartridge and to provide signal connections between the optical cartridge and host controller PCA 410 via backplane PCA 420.

Figure 5:
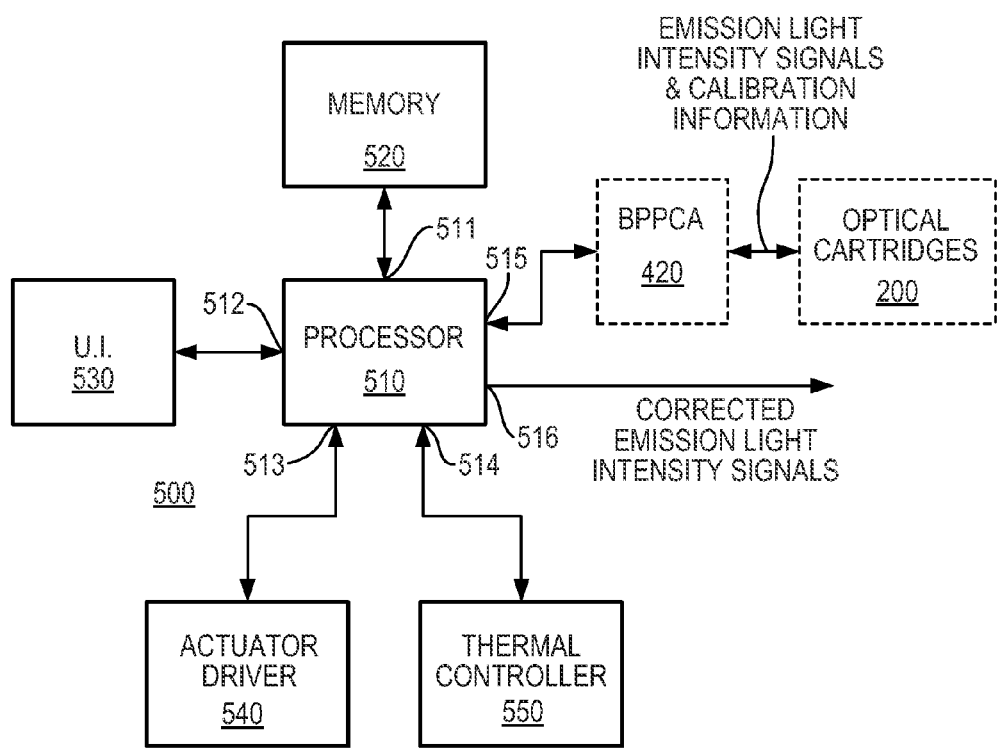
FIG. 5 is a block diagram showing an example of the circuitry of the host controller printed circuit assembly (PCA) of the host apparatus.

FIG. 5 is a block diagram showing an example 500 of the circuitry of host controller PCA 410 located in host apparatus 110. Host controller PCA 500 includes a processor 510, memory 520, a user interface and peripherals block 530, an actuator driver 540 and a thermal controller 550. In addition to storing data generated by the operations performed by processor 510, memory 520 additionally stores the calibration information received from each optical cartridge 200 installed in a respective optical cartridge receptacle 132 in stage 130. In the example shown, memory 520 is separate from processor 510. In other examples, memory 520 constitutes part of processor 510. Typically, memory 520 includes a non-volatile region in which are stored, for example, programs run by processor 510.

User interface and peripherals block 530 enables a user to input user commands to processor 510 and provides an interface through which system 100 can connect to other equipment. During operation of system 100, processor 510 generates control signals to control actuator driver 540 that drives actuator 150 to move stage 130 back and forth relative to well plate receptacle 122, as described above. Processor 510 additionally generates control signals to control well plate receptacle thermal controller 550 that controls a heater (not shown), and, in some embodiments, a cooler (not shown), that determine the temperature of well plate receptacle 122, and, hence, the temperature of well plate 10. Processor 510 additionally generates control signals to control the one or more optical cartridges 200 installed in respective optical cartridge receptacles 132 in the stage 130 of host apparatus 110.

Processor 510 has a memory interface 511, a user interface port 512, an actuator driver interface 513, a thermal controller interface 514, and optical cartridge interface 515 and an output port 516. Memory interface 511 is connected to memory 520 to output control signals and data to the memory and to receive data from the memory. User interface port 512 is connected to user interface and peripherals block 530 to exchange signals with the user interface. Actuator driver interface 513 is connected to actuator driver 540 to exchange signals with the actuator driver. Thermal controller interface 514 is connected to thermal controller 550 to exchange signals with the thermal controller. Optical cartridge interface 515 is connected via ribbon cable 412 and backplane PCA 420 to the one or more optical cartridges 200 installed in respective optical cartridge receptacles 132 of stage 130. Processor 510 exchanges control signals with the each optical cartridge installed in stage 130, receives respective calibration information from each optical cartridge installed in stage 130 and receives a respective emission light intensity signal from each optical assembly 210 of each optical cartridge 200 installed in stage 130. Processor 510 outputs at output port 516 a respective corrected light emission intensity signal for each optical assembly 210 of each optical cartridge 200 installed in stage 130.

Prior to system 100 performing measurements using a newly-installed optical cartridge, processor 510 instructs optical cartridge 200 via optical cartridge interface 515 and backplane PCA 420 to download respective calibration information for each optical assembly 210 of the optical cartridge. Processor 510 receives the calibration information at optical cartridge interface 515 and stores the calibration information in memory 520. Processor 510 stores the calibration information for each optical assembly 210 of optical cartridge 200 linked to an identifier of the optical assembly and an identifier of the optical cartridge receptacle 132 in which optical cartridge 200 is installed. The identifier could simply be a map that links the address in memory 520 where the calibration information is stored to an address of the optical assembly and an address of the optical cartridge receptacle to which the calibration information pertains.

During a measurement operation, processor 510 receives via optical cartridge interface 515 and backplane PCA 420 a respective emission light intensity signal for each optical assembly of the one or more optical cartridges installed in stage 130. Processor 510 corrects the emission light intensity signal received for each optical assembly 210 of each optical cartridge 200 using the respective calibration information for the optical assembly previously received from the optical cartridge and stored in memory 520. Processor 510 outputs corrected emission light intensity signals at its output port 516.

Figure 6:
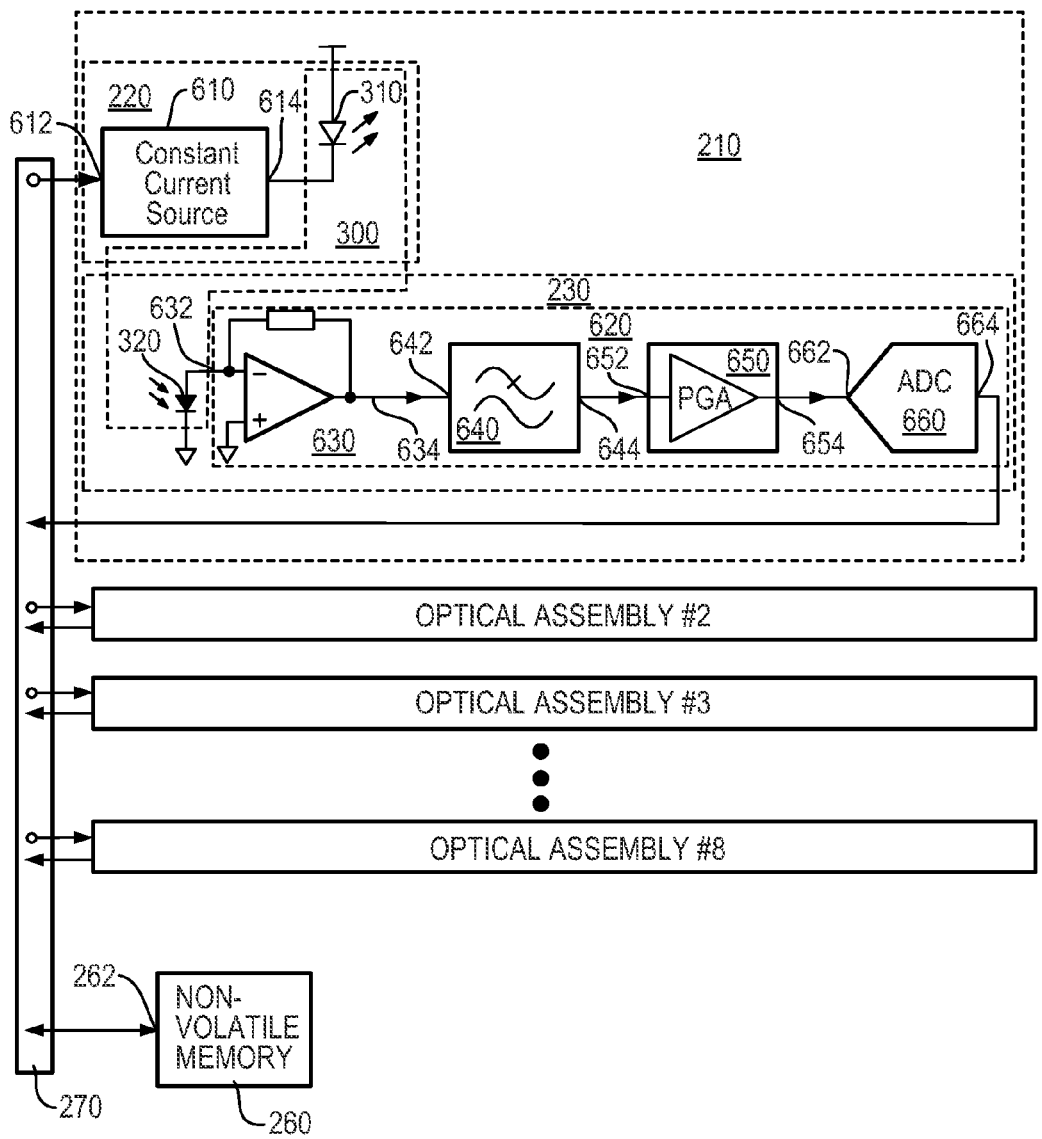
FIG. 6 is a block diagram showing an example of the circuitry of the optical cartridge.

FIG. 6 is a block diagram showing an example 600 of the circuitry located on printed circuit board 250 located in optical cartridge 200. Circuitry 600 includes circuitry associated with each optical module 300 of the optical cartridge and that, together with the optical module, constitutes a respective optical assembly 210. Circuitry 600 additionally includes circuitry that is common to all the optical assemblies 210 of optical cartridge 200. The per-optical assembly circuitry includes a current driver for the excitation light emitter 310 of the respective optical module 300 of each optical assembly and an amplifier and digitizer for the photocurrent generated by the emission light sensor 320 of the optical module. The common circuitry includes non-volatile memory 260 in which the calibration information for all the optical assemblies of the optical cartridge are stored. Connector 270 is mounted on printed circuit board 250 and is electrically connected to circuitry. 600 to provide power and to exchange signals.

Circuitry 600 within optical cartridge 200 is powered by host apparatus 110. To ensure the autonomy of optical cartridge 200, the analog portions of circuitry 600 located on printed circuit board 250 are configured in a way that makes their performance independent of the voltage or voltages of the power provided by host apparatus 110. This enables optical cartridge 200 to be calibrated independently of host apparatus 110, and allows optical cartridges to be swapped between host apparatuses without the need to recalibrate the optical cartridges.

Circuitry 600 includes a current driver 610 that drives excitation light emitter 310. Current driver 610 includes a current output 614 connected to output a defined drive current to excitation light emitter 310. In one version of excitation light source 220, each of the current drivers 610 on printed circuit board 250 outputs the same nominal drive current to its respective excitation light emitter 310. Driving all the excitation light sources 220 of the optical cartridge with the same nominal drive current results in differences in the intensity of the excitation light among the excitation light sources. However, as will be described in detail below, the differences in the intensity of the excitation light are corrected for during the process of calibrating the optical cartridge.

In another version of the excitation light source 220, current driver 610 is a programmable current driver having a control input 612. Control input 612 is connected to connector 270 to receive an intensity control signal from host apparatus 110. In this version, the intensity control signal is a common intensity control signal that is common to the current drivers 610 of all the optical assemblies 210 and simply defines the nominal current output of the current drivers 610, A common intensity control signal allows the current output of current drivers 610 to be set in accordance with the type of LED used as excitation light emitter 310. The drive current required to generate a given intensity of excitation light differs, for example, between LEDs of different colors, or between LEDs of the same color but of different efficacy. Driving all the excitation light emitters 310 in optical cartridge 200 with the same nominal drive current results in differences in the intensity of the excitation light among the excitation light sources. However, as will be described in detail below, the differences in the intensity of the excitation light are compensated for during the process of calibrating the optical cartridge.

In the example shown, current driver 610 is a programmable current driver having a control input 612. Control input 612 is connected to connector 270 to receive a respective individual intensity control signal determined during the calibration process. The individual intensity control signals enable the current outputs of the current drivers 610 to differ among the optical assemblies 210 to the extent necessary to make the excitation light sources of all the optical assemblies generate substantially the same intensity of excitation light.

Circuits that may be used as non-programmable or programmable versions of current driver 610 are known in the art and may be used.

Circuitry 600 additionally includes a detector circuit 620 to amplify and digitize the current generated by emission light sensor 320 of each optical assembly 210 in response to the emission light received at the respective light input/output port 380 of the optical assembly. In the example shown, detector circuit 620 includes a transconductance amplifier 630, a low-pass filter 640, an amplifier 650, and an analog-to-digital converter (ADC) 660.

Detector circuit 620 includes low-pass filter 640 to filter out high-frequency noise generated by transconductance amplifier 630. In an example, low-pass filter 640 has a cutoff frequency of 2 kHz and is a second-order low-pass filter. In the example shown, a programmable-gain amplifier is used as amplifier 650 to enable the gain of the amplifier to be set to match the dynamic range of the output signal of low-pass filter 640 (which depends on the dynamic range of the photocurrent generated by emission light sensor 320) to the input dynamic range of ADC 660. In other examples, a fixed-gain amplifier is used as amplifier 650.

Transconductance amplifier 630 has a current input 632 connected to receive the photocurrent generated by emission light sensor 320, and a voltage output 634. Low-pass filter 640 has an input 642 and an output 644. Input 642 is connected to voltage output 634 of transconductance amplifier 630. Amplifier 650 has an input 652 and an output 654. The input 652 of amplifier 650 is connected to the output 644 of low-pass filter 640. ADC 660 has an analog input 662 and a digital output 664. Analog input 662 is connected to the output 654 of amplifier 650. Digital output 664 is connected to electrical connector 270 to deliver to host apparatus 110 the emission light intensity signal that represents the photocurrent generated by emission light sensor 320 in response to the emission light incident thereon.

Circuitry 600 additionally includes a non-volatile memory 260. Non-volatile memory 260 has an input/output port 262 connected to connector 270 via which the non-volatile memory receives calibration information for each of the optical assemblies 210 constituting optical cartridge 200 for storage therein, and outputs calibration information stored therein to host apparatus 110. Non-volatile memory 260 additionally receives control signals, including addressing information, from host apparatus 110 via input/output port 262.

Optical cartridge 200 is calibrated using a calibration system (not shown) that, in some versions, includes a stage (not shown) on which a photometer (not shown) and a calibration light source (not shown) are mounted. The photometer is used to measure the intensity of the excitation light output by each of the optical assemblies of the optical cartridge being calibrated, and may also be used to monitor the intensity of the calibration light generated by the calibration light source. The calibration light source generates calibration light in a range of wavelengths within the pass band of the emission light bandpass filters 360 of the optical modules 300 of the optical cartridge, and with an intensity within the range of intensities of emission light that optical cartridge 200 is specified to measure. In some examples, the calibration light source generates the calibration light with a spectrum that emulates the spectrum of the emission light generated by the fluorescent dye with which optical cartridge 200 specified to operate. In some examples, the calibration light source sequentially generates the calibration light at different intensities within the range of intensities that optical cartridge 200 is specified to measure The calibration system (not shown) receives optical cartridge 200 with the surface 284 of the enclosure 280 of the optical cartridge facing the stage on which the photometer and the calibration light source are mounted. The calibration system includes an electrical connector (not shown) that connects to the electrical connector 270 of optical cartridge 200 to provide signal and power connections to the optical cartridge. The stage is movable longitudinally relative to optical cartridge 200 to selectively align the photometer or the light source mounted on the stage with the light input/output port 380 of the optical module 300 of each optical assembly 210 of optical cartridge 200 in turn.

The calibration process generates calibration information for each optical assembly 210 of optical cartridge 200. The calibration information is stored in the non-volatile memory 260 of the optical cartridge. The calibration information for each optical assembly 210 consists of at least a multiplier that is used by processor 510 on the host controller PCA 410 of host apparatus 110 to correct the emission light intensity signal generated by the emission light detector 230 of the optical assembly to generate a respective corrected emission light intensity signal. In embodiments of optical cartridge 200 in which the current drivers 610 are collectively programmable, the calibration information additionally includes the collective intensity control signal for the optical cartridge. In embodiments of optical cartridge 200 in which the current drivers 610 are individually programmable, the calibration information for each optical assembly 210 additionally includes the individual intensity control signal for the excitation light source 220 of the optical assembly.

In an example of using the calibration system to calibrate an example of optical cartridge 200, the stage of the calibration system is operated to align the photometer mounted on the stage with the light input/output port 380 of the optical module 300 of a first one of the optical assemblies 210 to be calibrated. At the start of the calibration process, the calibration system supplies power to the optical cartridge 200 being calibrated.

In embodiments of optical cartridge 200 in which current drivers 610 are not programmable, supplying power to the optical cartridge causes the excitation light sources 220 in the optical cartridge to generate excitation light. The photometer measures the intensity of the excitation light generated by the excitation light source 220 of the optical assembly 210 being calibrated and outputs to the calibration system an excitation light intensity signal that represents the measured intensity of the excitation light received from the optical assembly being calibrated. The calibration system divides the excitation light intensity signal by a target excitation light intensity signal to generate an excitation light calibration factor that the calibration system temporarily stores.

In embodiments of optical cartridge 200 in which the current drivers 610 are collectively programmable, at the beginning of the calibration process, the calibration system provides to the optical cartridge a collective intensity control signal that causes the excitation light sources 220 in the optical cartridge to generate excitation light having a nominal intensity defined by the intensity control signal. The process for determining the excitation light calibration factor for the optical assembly 210 being calibrated is the same as that described. The calibration system temporarily stores the resulting excitation light calibration factor.

In embodiments of optical cartridge 200 in which the current drivers 610 are individually programmable, the calibration system provides to the optical assembly 210 being calibrated an initial individual intensity control signal that causes the excitation light source 220 of the optical assembly being calibrated to generate excitation light at an initial intensity. The photometer measures the initial intensity of the excitation light and outputs to the calibration system a measured excitation light intensity signal that represents the measured initial intensity of the excitation light. The calibration system compares the measured excitation light intensity signal with a target excitation light intensity signal that represents the target intensity of the excitation light. When the measured excitation light intensity signal differs from the target excitation light intensity signal by greater than a specified tolerance, the calibration system changes the individual intensity control signal supplied to the optical assembly until the intensity control signal reaches a final state in which the difference between the measured excitation light intensity signal and the target excitation light intensity signal falls within the specified tolerance. The calibration system temporarily stores the final state of the intensity control signal for the optical assembly 210 being calibrated. In some versions, especially those in which the specified tolerance is relatively wide, the calibration system additionally divides the measured excitation light intensity signal obtained with the individual intensity control signal in its final state by the target excitation light intensity signal to generate an excitation light calibration factor for the optical assembly 210 being calibrated and the calibration system temporarily stores the excitation light calibration factor.

The calibration system then operates the stage to align its calibration light source with the light input/output port 380 of the optical module 300 of the optical assembly 210 being calibrated and causes the calibration light source to generate calibration light of a defined intensity. As noted above, some versions of the calibration system direct a portion of the calibration light generated by the calibration light source to the photometer and control the calibration light source to generate the calibration light with a defined intensity as measured by the photometer. Other versions use a separate photometer to measure the intensity of the calibration light generated by the calibration light source. In an example, the intensity of the calibration light generated by a calibration light source is in the middle of the range of intensities of emission light that optical cartridge 200 is specified to measure.

In response to the calibration light, the emission light detector 230 of the optical assembly 210 being calibrated generates a measured calibration light intensity signal that represents the intensity of the calibration light as measured by the emission light detector. The optical cartridge outputs the measured calibration light intensity signal to the calibration system. The calibration system divides the measured calibration light intensity signal by a target calibration light intensity signal that represents a target level of the calibration light intensity signal to generate an emission light calibration factor. Some versions of the calibration system calibrate emission light detector 230 at more than one intensity of the calibration light to generate an emission light calibration factor for each intensity of the calibration light.

The calibration system next retrieves the temporarily-stored excitation light calibration factor, and multiplies the excitation light calibration factor by the newly-generated emission light calibration factor to generate an overall calibration factor for the optical assembly 210 being calibrated. In versions in which the emission light detector 230 is calibrated at more than one intensity of the calibration light, the calibration system generates a respective calibration factor for each intensity of the calibration light as the calibration information for the optical assembly being calibrated.

The calibration system repeats the process just described for each of the remaining optical assemblies 210 of optical cartridge 200. Prior to making each set of measurements, the calibration system aligns its stage with the light input/output port 380 of the optical module 300 of the optical assembly 210 being calibrated.

Once it has generated a calibration factor for each optical assembly of optical cartridge 200, the calibration system uploads the calibration factors to the optical cartridge and causes the optical cartridge to store each calibration factor in non-volatile memory 260 as calibration information. Each calibration factor is stored in non-volatile memory 260 linked to an identifier of the optical assembly to which it pertains.

In embodiments of optical cartridge 200 in which current drivers 610 are collectively programmable, the calibration system additionally uploads the collective intensity control signal to the optical cartridge and causes the optical cartridge to store the collective intensity control signal in non-volatile memory 260 as calibration information.

In embodiments of optical cartridge 200 in which current drivers 610 are individually programmable, the calibration system additionally uploads the individual intensity control signals to the optical cartridge and causes the optical cartridge to store each intensity control signal in non-volatile memory 260 as calibration information. Each intensity control signal is stored in non-volatile memory 260 linked to an identifier of the optical assembly to which it pertains.

When optical cartridge 200 is installed in host apparatus 110 being calibrated as just described, the host apparatus causes optical cartridge 200 to read the calibration information stored in its non-volatile memory 260 and to download the calibration information to the host apparatus. Within host apparatus 110, the calibration information received from the optical cartridge is stored in memory 520 (FIG. 5) associated with (or part of) processor 510. The calibration information received from the optical cartridge is linked to an identifier of the optical cartridge receptacle 132 in which optical cartridge 200 is installed. Additionally, calibration information that pertains to a specific optical assembly 210 of optical cartridge 200 is stored in memory 520 linked to an identifier of that optical assembly.

When system 100 is used to perform fluorescence measurements using optical cartridge 200, processor 510 instructs actuator driver 540 to cause actuator 150 to move stage 130 until the light input/output ports 380 of the optical assemblies 210 of optical cartridge 200 are aligned with a designated group of wells 20 (i.e., a row or column of wells, depending on the orientation of well plate 10 relative to the direction of movement of stage 130) of well plate 10.

In embodiments of optical cartridge 200 in which current drivers 610 are collectively programmable, processor 510 reads the collective intensity control signal pertaining to optical cartridge 200 from memory 520 and outputs the collective intensity control signal for upload to optical cartridge 200. In optical cartridge 200, the collective intensity control signal defines the intensity of the excitation light output by all the optical assemblies 210 of the optical cartridge.

In embodiments of optical cartridge 200 in which current drivers 610 are individually programmable, processor 510 reads the individual intensity control signal for each optical assembly 210 of optical cartridge 200 from memory 520 and outputs the individual intensity control signals for upload to optical cartridge 200. In optical cartridge 200, each individual intensity control signal defines the intensity of the excitation light output by its respective optical assembly.

The fluorescent dye in the wells 20 aligned with optical cartridge 200 is irradiated by the excitation light output by the optical assemblies 210 of optical cartridge 200. The emission light stimulated by the excitation light is detected by the emission light detectors 230 of the optical assemblies 210 of optical cartridge 200 to generate respective emission light intensity signals. Optical cartridge 200 outputs the emission light intensity signals to host apparatus 110, specifically to processor 510. Each emission light intensity signal is linked to an identifier of the optical assembly of optical cartridge 200 from which it originated. Processor 510 divides the emission light intensity signal for each optical assembly by the respective calibration factor for the optical assembly retrieved from the memory 520 associated with processor 510 to generate a respective corrected emission light intensity signal that the processor outputs at its output port 516.

Referring again to FIGS. 1A and 1B, some embodiments of host apparatus 110, such as those intended for qPCR reactions, include a heater (not shown) thermally coupled to well plate receptacle 122. Other embodiments of host apparatus 110 additionally or alternatively include a cooler (not shown) thermally coupled to well plate receptacle 122 to control the temperature of the well plate receptacle. The heater and/or cooler is controlled by well plate receptacle thermal controller 550 (FIG. 5).

In the example shown, actuator 150 moves stage 130 relative to well plate receptacle 122 along a pair of rails 160 that extend across chassis 120. One of the rails 160 is located near the front of the chassis and the other of the rails 160 is located near the rear of the chassis. In the example shown, stage 130 is slidably mounted on rails 160. In other examples, wheels or rollers (not shown) are mounted on the stage and the wheels or rollers run on the rails. Other ways of mounting stage 130 relative to well plate receptacle 122 in a manner that allows stage 130 and well plate receptacle 122 to move relative to one another in a direction parallel to the wells along one axis of the array of wells in well plate 10 mounted in well plate receptacle 122 exist may be used. In the example shown, well plate receptacle 122 is statically mounted on chassis 120 and actuator 150 moves stage 130 laterally relative to well plate receptacle 122 along rails 160. In other examples (not shown), stage 130 is statically mounted on chassis 120 and actuator 150 moves well plate receptacle 122 laterally relative to stage 130 along rails 160.

In the example shown, actuator 150 includes a motor 152, typically a stepper motor, mounted on chassis 120 near one side. The output shaft of motor 152 is fitted with a toothed pulley 154. Another pulley 156, which, in some embodiments, is toothed, is mounted on chassis 120 at the other side of the chassis opposite toothed pulley 154. An endless toothed belt 158 wraps around toothed pulleys 154, 156 and is affixed to stage 130 part-way along its length. Rotation of the output shaft of motor 152 moves stage 130 relative to well plate receptacle 122 in the x-direction parallel to the rows of wells 20 in well plate 10 mounted in well plate receptacle 122.

This disclosure describes the invention in detail using illustrative embodiments. However, the invention defined by the appended claims is not limited to the precise embodiments described.

We claim:

1. A fluorescence measurement system for performing fluorescence measurements on a multi-well well plate having wells arranged in a rectangular array having a first axis and a second axis, orthogonal to the first axis, the system comprising:

a host apparatus, comprising:
a well plate receptacle to locate the well plate; and
a stage comprising an optical cartridge receptacle, the optical cartridge receptacle elongate in a first direction, parallel to the first axis of the well plate received by the well plate receptacle, the optical cartridge receptacle comprising an electrical connector at a surface thereof, in which at least one of the stage and the well plate receptacle is movable relative to the other of the stage and the well plate receptacle in a second direction, parallel to the well plate and to the second axis of the well plate;

a self-contained, multichannel optical cartridge configured to engage with the optical cartridge receptacle, the optical cartridge comprising:
   a linear array of optical assemblies, each of the optical assemblies comprising a respective excitation light source to generate excitation light for output to a respective well of the well plate and a respective emission light detector to generate an emission light intensity signal in response to emission light received from the respective well of the well plate,
   a memory to store respective calibration information for each of the optical assemblies, and
   an electrical connector electrically coupled to the memory and to each of the optical assemblies and configured to connect to the electrical connector of the optical cartridge receptacle;
in which the host apparatus additionally comprises a processor to correct the emission light intensity signal received from each optical assembly of the optical cartridge using the respective calibration information received from the optical cartridge for the optical assembly.

2. The system of claim 1, in which:
the optical cartridge receptacle is a first optical cartridge receptacle;
the stage additionally comprises second optical cartridge receptacle offset from the first optical cartridge receptacle in the second direction; and
the optical cartridge is configured to engage with any one of the optical cartridge receptacles.

3. The system of claim 2, in which:
the optical cartridge is a first optical cartridge;
the system additionally comprises a second optical cartridge; and
the first optical cartridge and the second optical cartridge are each configured to engage with any one of the optical cartridge receptacles.

4. The system of claim 1, in which the stage moves relative to the well plate receptacle in the second direction.

5. The system of claim 1, in which each of the optical assemblies additionally comprises:
a beam splitter;
a collimating lens and an excitation light bandpass filter between the excitation light source and the beam splitter; and
a focusing lens and an emission light bandpass filter between the emission light detector and the beam splitter.

6. The system of claim 5, in which the beam splitter transmits the emission light and reflects the excitation light.

7. The system of claim 5, in which the beam splitter reflects the emission light and transmits the excitation light.

8. The system of claim 5, in which the beam splitter is a dichroic beam splitter.

9. The system of claim 5, in which the excitation light bandpass filter and the emission light bandpass filter have respective pass bands having a respective center wavelengths that differ from one another.

10. The system of claim 5, in which:
the optical cartridge is a first optical cartridge; and
the system additionally comprises a second self-contained, multichannel optical cartridge configured to engage with any one of the optical cartridge receptacles, and comprising a linear array of optical assemblies, the optical assemblies of the second optical cartridge differing from those of the first optical cartridge in that at least one of the excitation light bandpass filter and the emission light bandpass filter of the second optical cartridge differs in center wavelength from a corresponding one of the excitation light bandpass filter and the emission light bandpass filter of the first optical cartridge.

11. The system of claim 10, in which the first optical cartridge and the second optical cartridge are engaged with respective optical cartridge receptacles in the stage.

12. The system of claim 1, in which:
each of the optical assemblies additionally comprises a respective light source driver to provide current to the excitation light source in response to an intensity control signal that additionally constitutes part of the calibration information; and
the processor of the host apparatus is additionally to extract a common intensity control signal from the calibration information received from the optical cartridge, and to output the common intensity control signal to the light source drivers of all the optical assemblies of the optical cartridge.

13. The system of claim 1, in which:
each of the optical assemblies additionally comprises a respective light source driver to provide current to the excitation light source in response to an intensity control signal that additionally constitutes part of the calibration information; and
the processor of the host apparatus is additionally to extract individual intensity control signals from the calibration information received from the optical cartridge, and to output a respective one of the individual control signals to the respective light source driver of each of the optical assemblies of the optical cartridge.

14. The system of claim 1, in which:
the calibration information for each optical assembly comprises a calibration factor; and
the processor of the host apparatus is additionally to divide the emission light intensity signal output by each optical assembly by the respective calibration factor for the optical assembly.

15. The system of claim 1, in which the optical assemblies correspond in number to the wells along the first axis of the well plate.

16. The system of claim 1, additionally comprising a heater to heat the well plate receptacle.

17. A self-contained, multichannel optical cartridge for installation into a host apparatus to perform fluorescence measurements on a multi-well well date having wells arranged in a linear array in which the wells are offset from one another by a pitch, the optical cartridge comprising:
optical assemblies arranged in a linear array, and offset from one another by a pitch equal to the pitch of the wells, each of the optical assemblies comprising:
   a respective excitation light source to generate excitation light for output from the optical cartridge,
   a respective light source driver to provide current to the excitation light source in accordance with an intensity control signal, and
   a respective emission light detector to generate an emission light intensity signal in response to emission light received by the optical cartridge, the emission light differing in wavelength from the excitation light and superposed thereon;
a memory to store respective calibration information for each of the optical assemblies, the calibration information comprising an intensity control signal; and
an electrical connector at a surface of the optical cartridge, the electrical connector providing electrical connections comprising:

an electrical connection to output the calibration information stored in the memory of the optical cartridge to the host apparatus, an electrical connection to receive the intensity control signal from the host apparatus, and a respective electrical connection to output the emission light intensity signal from the emission light detector of each of the optical assemblies to the host apparatus.

18. The optical cartridge of claim 17, in which each of the optical assemblies additionally comprises:

a beam splitter;

a collimating lens and an excitation light bandpass filter between the excitation light source and the beam splitter; and a focusing lens and an emission light bandpass filter between the emission light detector and the beam splitter.

19. The optical cartridge of claim 18, in which the beam splitter transmits the emission light and reflects the excitation light.

20. The optical cartridge of claim 18, in which the beam splitter reflects the emission light and transmits the excitation light.

21. The optical cartridge of claim 18, in which the beam splitter is a dichroic beam splitter.

22. The optical cartridge of claim 18, in which the excitation light bandpass filter and the emission light bandpass filter have respective pass bands having respective center wavelengths that differ from one another.

* * * * *

UNITED STATES PATENT AND TRADEMARK OFFICE
CERTIFICATE OF CORRECTION

| | | |
|---|---|---|
| PATENT NO. | : 8,858,886 B1 | Page 1 of 1 |
| APPLICATION NO. | : 13/890047 | |
| DATED | : October 14, 2014 | |
| INVENTOR(S) | : Yuen Chang Chuah et al. | |

It is certified that error appears in the above-identified patent and that said Letters Patent is hereby corrected as shown below:

In the Claims
In column 20, line 46, In Claim 17, delete "date" and insert -- plate --, therefor.

Signed and Sealed this
Third Day of March, 2015

Michelle K. Lee
*Deputy Director of the United States Patent and Trademark Office*